(12) United States Patent
Solem

(10) Patent No.: US 10,779,933 B2
(45) Date of Patent: Sep. 22, 2020

(54) DEVICE, SYSTEM AND METHOD FOR ANCHORING TO MUSCLE TISSUE

(71) Applicant: Syntach AG, Schaffhausen (CH)

(72) Inventor: Jan Otto Solem, Bjärred (SE)

(73) Assignee: Syntach AG, Schaffhausen (CH)

(*) Notice: Subject to any disclaimer, the term of this patent is extended or adjusted under 35 U.S.C. 154(b) by 0 days.

(21) Appl. No.: 15/537,882

(22) PCT Filed: Dec. 22, 2015

(86) PCT No.: PCT/EP2015/080968
§ 371 (c)(1),
(2) Date: Jun. 19, 2017

(87) PCT Pub. No.: WO2016/102561
PCT Pub. Date: Jun. 30, 2016

(65) Prior Publication Data
US 2017/0340436 A1    Nov. 30, 2017

(30) Foreign Application Priority Data

Dec. 22, 2014    (EP) .................................... 14199913

(51) Int. Cl.
*A61F 2/08* (2006.01)
*A61F 2/24* (2006.01)
(Continued)

(52) U.S. Cl.
CPC .............. *A61F 2/0811* (2013.01); *A61F 2/08* (2013.01); *A61F 2/2478* (2013.01);
(Continued)

(58) Field of Classification Search
CPC ........ A61F 2002/0894; A61F 2002/249; A61F 2/2478
See application file for complete search history.

(56) References Cited

U.S. PATENT DOCUMENTS

2005/0087620 A1    4/2005 Bowers et al.
2005/0197696 A1    9/2005 Duran
(Continued)

FOREIGN PATENT DOCUMENTS

CN    102821702 A    12/2012
CN    102939059 A    2/2013
(Continued)

OTHER PUBLICATIONS

WIPO, European International Search Authority, International Search Report and Written Opinion dated Aug. 3, 2016 in International Patent Application No. PCT/EP2015/080968, 12 pages.
(Continued)

*Primary Examiner* — Christine H Matthews
(74) *Attorney, Agent, or Firm* — Inskeep IP Group, Inc.

(57) ABSTRACT

An implant for assisting contraction and/or extension of a muscle that includes a stem with an adhesion resistant segment and an anchoring segment wherein at least a portion of each of the adhesion resistant segment and the anchoring segment is configured to be implantable within a muscle and the anchoring segment is positioned on a distal portion of the stem and the adhesion resistant segment is positioned proximally on the stem relative to the anchoring segment.

18 Claims, 6 Drawing Sheets

(51) Int. Cl.
*A61M 1/10* (2006.01)
*A61M 1/12* (2006.01)

(52) U.S. Cl.
CPC ........ *A61M 1/1012* (2014.02); *A61M 1/1034* (2014.02); *A61F 2002/0894* (2013.01); *A61F 2002/249* (2013.01); *A61M 1/1008* (2014.02); *A61M 1/1068* (2013.01); *A61M 1/1086* (2013.01); *A61M 1/12* (2013.01)

(56) References Cited

U.S. PATENT DOCUMENTS

| 2006/0195012 | A1 | 8/2006 | Mortier | |
|---|---|---|---|---|
| 2007/0118151 | A1* | 5/2007 | Davidson | A61B 17/00234 606/144 |
| 2008/0082130 | A1 | 4/2008 | Ward | |
| 2010/0161041 | A1 | 6/2010 | Maisano et al. | |
| 2012/0190918 | A1 | 7/2012 | Oepen et al. | |
| 2012/0245678 | A1* | 9/2012 | Solem | A61M 1/127 623/2.36 |

FOREIGN PATENT DOCUMENTS

| WO | WO2007-100408 A2 | 9/2007 |
|---|---|---|
| WO | WO2007/131513 A1 | 11/2007 |
| WO | WO2009/081396 A2 | 7/2009 |
| WO | WO2011/097355 A2 | 8/2011 |
| WO | WO2011/119101 A1 | 9/2011 |
| WO | WO2013/049682 A1 | 4/2013 |

OTHER PUBLICATIONS

WIPO, WO2011/097355A3, Korean International Search Authority, International Search Report dated Oct. 17, 2011 in International Patent Application No. PCT/US2011/023568, 5 pages.

* cited by examiner

DEVICE, SYSTEM AND METHOD FOR ANCHORING TO MUSCLE TISSUE

RELATED APPLICATIONS

This application is the U.S. National Phase of and claims priority to International Patent Application No. PCT/EP2015/080968, International Filing Date Dec. 22, 2015, entitled Device, System And Method For Anchoring To Muscle Tissue; which claims benefit of European Application No. 14199913.6 filed Dec. 22, 2014 entitled Device, System And Method For Anchoring To Muscle Tissue; both of which are incorporated herein by reference in their entireties.

BACKGROUND OF THE INVENTION

Field of the Invention

The present invention relates generally to apparatus and methods for anchoring to muscle tissue, especially cardiac and skeletal muscle tissue, and systems for moving or assisting natural movement of muscle.

Description of the Prior Art

Diseases and injury can damage heart and skeletal muscle, leading to the need for apparatus and methods for assisting heart and/or skeletal muscle function. For example, high blood pressure can lead to cardiac muscle hypertrophy and congestive heart failure. Atherosclerosis can cause myocardial infarction, resulting in the death of heart muscle tissue. ALS or nerve damage can lead to skeletal muscle weakness or paralysis. Apparatus and methods for assisting skeletal or heart muscle contraction to mitigate the above conditions and others, including smooth muscles, have been described and typically comprise an anchor that attaches a moving means to the muscle so that the muscle may be mechanically contracted or assisted in contraction by other muscles. Apparatus and methods exist for repairing attachments of muscle to tendon exist that comprise muscle anchors for reattaching tendon to skeletal muscle or for connecting muscles to artificial tendons.

For example US 2008/0082130 A1 discloses an apparatus designed to address a need for improved helical type coil anchors for tendon and ligament repair that allow for greater tensile loads and smaller anchor sizes. The apparatus comprises an elongate tensile member, such as a suture, adapted to extend within the interior of muscle or tendon tissue and a helical anchor configured for insertion within the interior of the muscle or tendon. A drive member coupled with the helical anchor rotates the helical anchor into the muscle or gathers tendon tissue onto the anchor. The tensile member can be connected to the helical anchor and placed under tension while repairing the muscle or tendon.

US 2010/0161041 A1 discloses an apparatus for repairing an atrioventricular valve comprising a helical anchor that is screwed into heart papillary muscle to attach repair chords, such as sutures, wires, or elongate tensioning coils, to the muscle. The repair chords can then function as artificial chordae tendineae.

WO 2009/081396 A2 discloses an apparatus for treating a heart comprising at least one anchor on an elongate tensioning element, such as a suture or filament, and adapted to couple the tension element to cardiac muscle tissue. The elongate tensioning element is delivered though a delivery tube with a sharp tip adapted to be pushed through cardiac muscle.

WO 2011/119101 discloses a medical device and method for enhancing intracardiac blood circulation by assisting left ventricular pump action. The device may comprise anchors for anchoring to cardiac muscle that may be, for example, in the form of hooks or blades, a left atrial appendage occluder, a septal occluder, or a foldable anchor for attachment to a mitral valve annulus with sutures. The anchors are used with a displacement unit that pulls on or pushes against the anchors to assist heart muscle movement.

Existing anchors and anchoring systems like those described above suffer from certain disadvantages that limit their effectiveness in certain applications. For example, an anchor attached to a muscle, when used for assisting the contraction of the muscle may cause the muscle to bend or roll in an unnatural way to limit the intended effect of muscle contraction and/or interfere with the normal function of the muscle. An anchor that embeds within a muscle by mechanical means causes scarring and/or immunological responses that may interfere with the normal function of the muscle. Anchoring systems comprising tensioning elements that pull on the muscle to assist contraction are not able to assist muscle relaxation or lengthening of the muscle because the tensioning elements are not able to apply pushing as well as pulling forces on the muscle. Mechanical anchors used for immediate anchoring are often made of materials that may become brittle or otherwise lose structural integrity over time. Anchors relying on tissue adhesion or ingrowth do not provide immediate anchoring to the muscle.

There is therefore a need in the art for improved muscle anchors and anchoring systems that can prevent muscle deformation during assisted muscle contraction and/or help support the muscle during contraction, especially in a direction that is lateral to contraction. There is also a need for improved muscle anchors and anchoring systems that apply forces to muscle that assist natural movement of muscle during muscle contraction and/or during muscle relaxation, and/or provide both immediate and long term anchoring.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device, a system, and a method according to the appended patent claims.

In one aspect, the disclosure provides a muscle implant comprising a stem having a segment that is resistant to adhesion to muscle tissue and having an anchoring segment that anchors the stem within a muscle is described. "Adhesion resistant" in this context describes a property resulting from a means of adhesion resistance on an adhesion resistant segment or surface which, once the implant is implanted in a muscle, prevents surrounding tissue from adhering to or forming adhesions with the adhesion resistant segment or surface and prevents tissue ingrowth into or onto the adhesion resistant segment or surface.

In another aspect, the disclosure provides a method for implanting an implant into a muscle.

In yet another aspect, the disclosure provides a system comprising an anchoring implant and a means for applying one or more forces to the implant to assist a contraction and/or a relaxation of a muscle.

In an additional aspect, the disclosure provides a method for delivering and assembling sections of a catheter delivered device in a catheter or at the site of implantation.

In a further aspect, the disclosure provides a method for assisting movements of a muscle, using an implant.

Further aspects of the disclosure are defined in the dependent claims, wherein features for the second and subsequent aspects of the invention are as for the first aspect mutatis mutandis.

The term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings.

DESCRIPTION OF PREFERRED EMBODIMENTS

Figure 1:
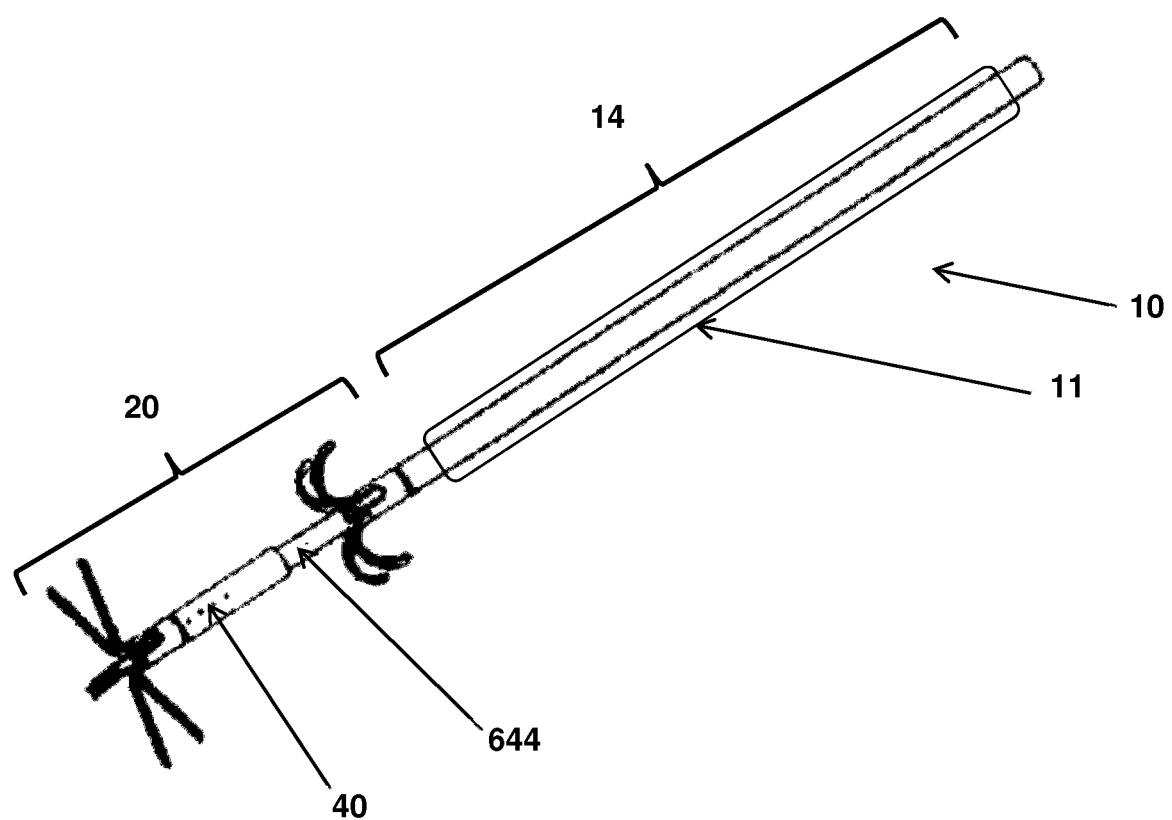
FIG. 1 is a schematic illustration of an embodiment of a muscle anchoring implant according to the invention.

Specific embodiments of the invention are described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 2:
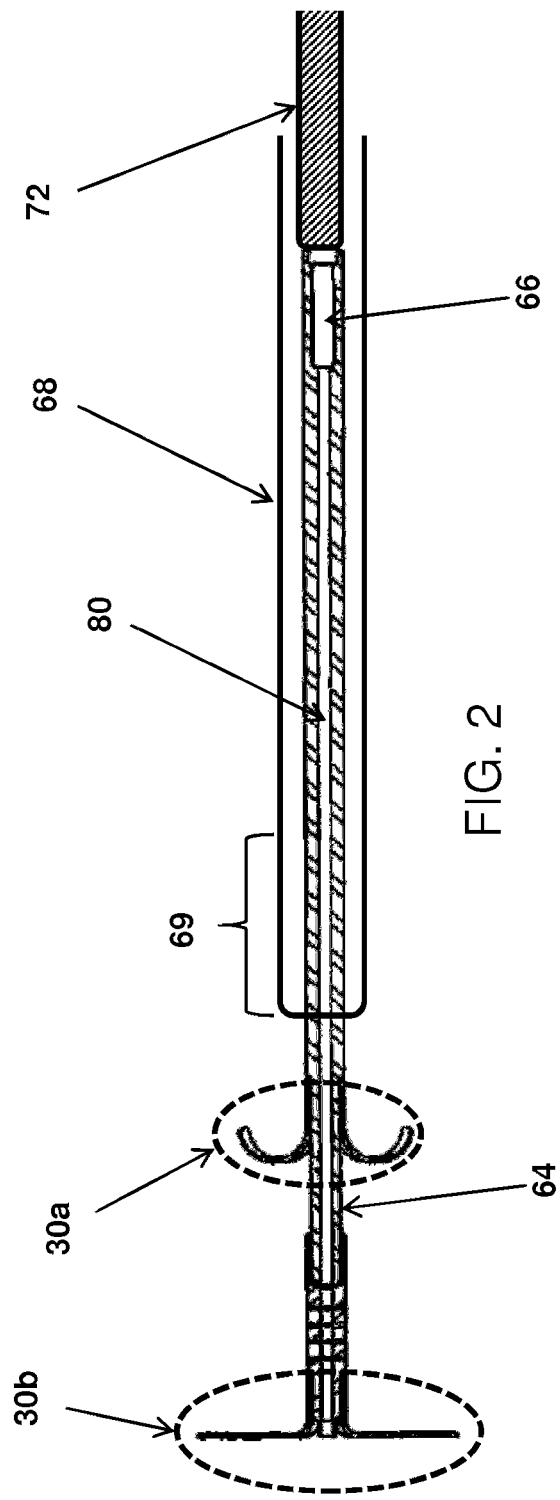
FIG. 2 is a schematic illustration of an embodiment of a muscle anchoring implant according to the invention including a delivery system.
Figure 3:
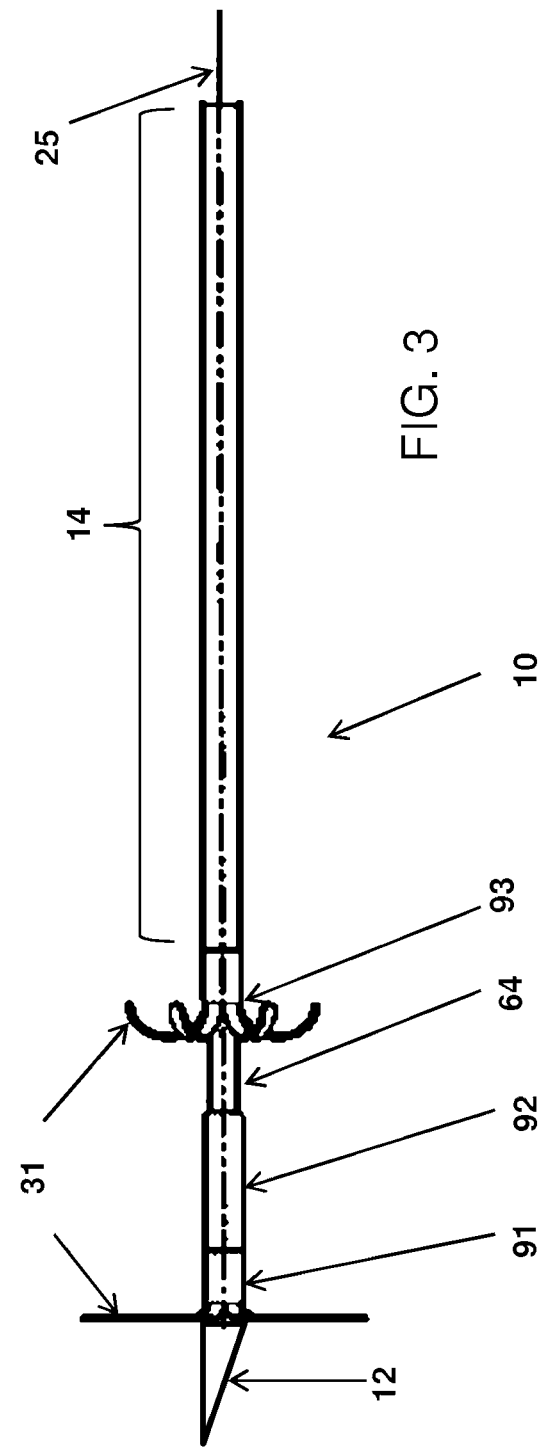
FIG. 3 is a schematic illustration of an embodiment of a muscle anchoring implant according to the invention having a segmented structure.
Figure 8:
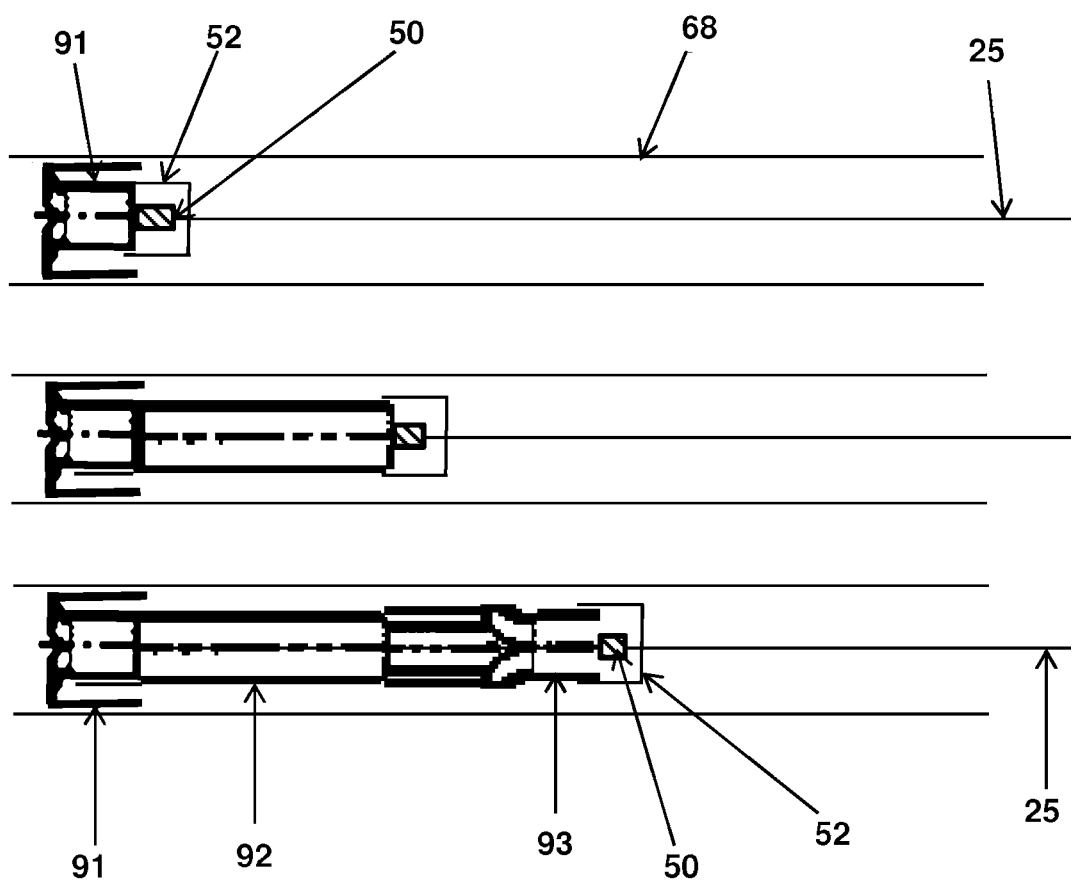
FIG. 8 is a schematic illustration of an embodiment of a muscle anchoring implant configured for assembly at least partially within a catheter.

Different embodiments of a muscle anchoring implant according to the present invention are shown in FIGS. 1-3. The implant comprises a stem (10), comprising an adhesion resistant segment (14) and a an anchoring segment (20). The stem (10) may comprise a single, monolithic core along its entire length, or a portion thereof, with components such as anchoring segments (30a, 30b) fixed to the core, for example, by welding, gluing, clamping, or force fitting attachment. Additionally or alternatively, the stem (10) can be made by connecting separate sections (91, 92, 93) to a distal end of the stem (10) by, for example, gluing, threaded attachment, clamping, welding, or force fitting attachment. The separate sections (91, 92, 93) may be connected to the distal end of the stem (10) sequentially or they may be connected to one another before attachment to the distal end of the stem. FIG. 3 shows three separate sections (91, 92, 93) connected to a distal end of the stem (10) with the three separate sections making up the anchoring segment. Other embodiments may comprise the same or different numbers of separate segments arranged differently along the length of the anchoring implant. In some embodiments the stem (10) may comprise two or more separate segments with at least one connection between segments that is reversible so that all or a portion of the adhesion resistant segment (14) of the stem (10) may be detached from the remainder of the stem (10) and removed from the muscle, leaving the anchoring segment (20) in the muscle. In some embodiments the stem (10) may comprise two or more separate segments with at least one connection between segments that is reversible so that all of the adhesion resistant segment (14) of the stem (10) and a portion of the anchoring segment (20) may be detached from the remainder of the stem (10) and removed from the muscle, leaving a portion of the anchoring segment (20) in the muscle. The separate sections may be assembled into a complete anchoring implant before delivery or during delivery within the lumen of a catheter (FIG. 8).

The stem (10) preferably has a central lumen (80) configured to fit over a guide wire (25) to facilitate the delivery of the stem to a target location in a muscle. Additionally or alternatively, the stem (10) may have a sharp or pointed distal end (12) allowing the stem to penetrate a muscle to position the anchoring segment (20) at a target position inside the muscle. Penetrating into muscle of the left ventricle, for example, may require penetrating an endocardium layer, an epicardium layer, and muscle facia. The stem (10) may be made rigid enough so that a pushing force for assisting the relaxation or lengthening of the muscle applied to the proximal end of the stem toward the distal end of the stem does not cause the stem to buckle within the muscle into which it is implanted. This feature allows the stem (10) to transfer a pushing force applied to the implant to the attachment point of the muscle and thereby assist muscle relaxation, or lengthening of the muscle.

Figure 7:
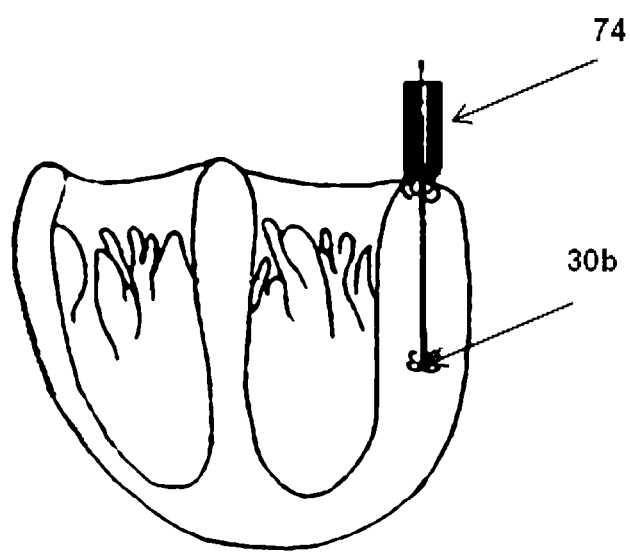
FIG. 7 is a schematic illustration of an embodiment of a muscle anchoring implant anchored in the muscle of the left ventricle of a human heart and attached to an actuator.

The proximal end of the stem (10) may comprise a connecting element (66) configured to provide reversible or permanent connection to a component of a delivery system such as a pushing/pulling rod (72) as shown in FIG. 2, a guide wire (25), and/or to an actuator (74) as shown in FIG. 7. In some embodiments, the connecting element (66) comprises means for reversible connection such as a threaded attachment, a knob or similar shape for reversible clamping, by a component of a delivery system or actuator (74) or by other known means for reversible attachment used with medical devices. In other embodiments, the connecting element (66) may be permanent connection means such as hooks, barbs, sutures, or other known means for permanent attachment used with medical devices. In yet other embodiments, the connecting element (66) may comprise both reversible and irreversible connections means such as attachment means configured for reversible attachment to a pushing rod (72) and irreversible connecting means to a guide wire (25) or an actuator (74).

The anchoring segment (20) is positioned at the distal portion of the stem (10) and is designed to anchor the stem to muscle tissue. The adhesion resistant segment (14) of the stem is designed to resist adhesion to muscle tissue so that muscle tissue in contact with the adhesion resistant segment (14) can move relative to the stem (10). When implanted inside a muscle, the stem (10) may have the effect of preventing the muscle from bending, folding, and/or buckling when a pulling force is applied through the stem to a portion of the muscle to which the anchoring segment is affixed. The stem (10) may be straight as shown in FIG. 1 or all or a part of the stem may be curved, for example, to accommodate the shape or natural movement of a muscle into which the implant is placed.

Resistance to adhesion to muscle tissue may be accomplished in several ways. For example, in one embodiment, the adhesion resistant segment (14) of the stem (10) may preferably be made of polished stainless steel. In another embodiment, the adhesion resistant segment (14) may comprise a material provided with an outer surface made of polished stainless steel. In other embodiments, the outer surface of the adhesion resistant segment (14) may be covered by a flexible membrane, fabric, or sleeve (11) that, even if adhered to muscle tissue, provides means for movement of the muscle tissue relative to the stem by allowing for movement between the stem (10) and the membrane, fabric, or sleeve. The flexible membrane, fabric, or sleeve is preferably fluid tight and made from one or a combination of physiologically compatible materials such as, silicon or other biocompatible polymers such as polyurethanes, polycarbonate urethanes, polyether urethanes, polyethylenes, or polyfluoroethylenes.

All or a portion of the stem (10) may be bendable, flexible or conditionally flexible. For example, in one embodiment the stem may be made of polished stainless steel having a cross-section that allows the stem (10) to flex during implantation and/or after being implanted into muscle. In another embodiment, the cross-sectional dimension and shape of the stem may vary to allow the stem to have different flexibilities and/or directions of flexibility in different sections of the stem. Additionally or alternatively, the cross section of the stem may be selected to allow the stem to flex in response to forces produced on the stem by the contraction of the particular muscle tissue into which the stem is implanted. The stem (10) may be at least partly comprised of a flexible material such as stainless steel and/or a biocompatible polymer comprising, for example, a polyamide, a polycarbonate, a polypropylene, a polyurethane, polyether ether ketone (PEEK), or any combinations thereof. Flexibility of the stem (10) may advantageously prevent or minimize the extent to which the stem resists or interferes with natural muscle movement. This feature is particularly useful when a muscle implant according to the invention is implanted in a functioning muscle for which a natural contraction is to be assisted.

Figure 4:
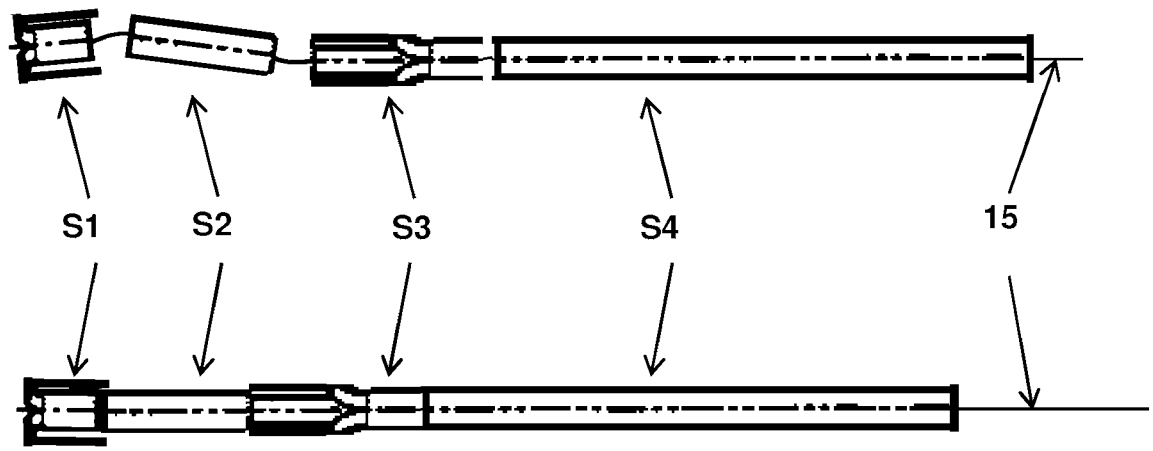
FIG. 4 is a schematic illustration of an embodiment of a muscle anchoring implant that is controllably flexible.

Conditional flexibility of the stem (10) means that the stem is flexible under one condition and less flexible or inflexible under another condition (FIG. 4). In some embodiments, the stem (10) may comprise structural sections (S1-S4) that are connected by one or more wires (15) running longitudinally along and/or within the structural sections and connected to the distal most structural section. During implantation, some or all of the sections may be loosely connected to allow movement at the interfaced of the structural sections. The configuration of the stem can then be fixed by restraining the structural sections by applying tension to the one or more wires while applying a pressure to the proximal end of the stem. The structural sections (S1-S4) may optionally be fixed to one another by, for example, threaded attachment, clamping, or force fitting attachment. Conditional flexibility may also be accomplished, for example, by structural sections (S1-S4) linked by lockable joints.

FIG. 4 shows four structural sections as an example. The number of structural sections and the functional components such as functional portions of the anchoring section (20) and adherence resistant segment (14) associated with each of the sections may be different for different embodiments. The embodiment shown in FIG. 4 is in a delivery shape for delivery through a catheter (not shown) with first and third structural sections (S1 and S3) each being mechanical anchors in a collapsed state. A shift from a flexible condition to a fixed condition may take place after one or more of the structural sections (S1-S4) is released from a delivery catheter and before or after each of anchor sections S1 and S3 is expanded to penetrate into muscle tissue. In some embodiments, some or all of the structural sections may be made by a three-dimensional printing process to produce a stem that is customized for a particular muscle of an individual patient, such as the left ventricle, or a skeletal muscle.

The anchoring portion (20) of the stem may be designed to provide immediate mechanical anchoring of the stem (10) to muscle tissue and/or anchoring by tissue adhesion and ingrowth. Mechanical anchoring provides immediate anchoring of the stem to muscle upon placement of the implant into muscle tissue. Immediate mechanical anchoring may be achieved, for example, by one or more mechanical anchors (30a, 30b) as illustrated for the embodiments shown in FIGS. 1-4. Other embodiments may comprise only one mechanical anchor (30a or 30b) or more than two mechanical anchors.

The mechanical anchors (30a, 30b) may anchor to an outer surface of a muscle and/or to an interior of a muscle from the inside of the muscle. The number and locations of mechanical anchors (30a, 30b) may vary depending on the muscle into which the implant is placed and desired functional characteristics of the anchor as described in more detail below. For anchoring from within the muscle, a mechanical anchor (30a, 30b) may comprise anchoring elements (31) such as barbs, hooks, rods, bars, or any combination of these. Such anchoring elements (31) are generally configured to be radially compact during the delivery of the implant into a muscle and then to expand radially to engage and penetrate muscle tissue surrounding the mechanical anchor.

The stem (10) may comprise one or more sections of reduced diameter (64) to accommodate anchoring elements (31) in a compact delivery conformation. This feature may allow the diameter of the stem (10) to be substantially constant along its length when the mechanical anchors (30a, 30b) are in a delivery conformation.

The anchoring elements shown in FIG. 3 are arranged so that they radiate from a single cross-sectional plane of the anchoring segment (20) but this is not required. The anchoring elements (31) may be arranged in other configurations for example where the anchoring elements (31) project from the anchoring segment (20) from different axial positions along the anchoring segment. The anchoring elements (31) of the embodiment shown in FIG. 4 are shown as extending either perpendicularly from the stem or curling in a proximal direction toward the proximal end of the stem. Other embodiments may comprise one or more mechanical anchors in which some or all of the anchoring elements curl toward the distal end of the stem. The number and orientation of anchoring elements (31) may also be different from those shown in the figures and may be shaped to provide immediate anchoring to withstand a pushing force applied to the stem toward the distal end of the stem and/or a pulling force applied to the stem in an opposite direction. The anchoring elements (31) may be made from a shape memory metal such as nitinol and/or a super elastic material such as nitinol or (Ti—Zr)—Mo—Sn biomedical superelastic alloys.

Figure 5:
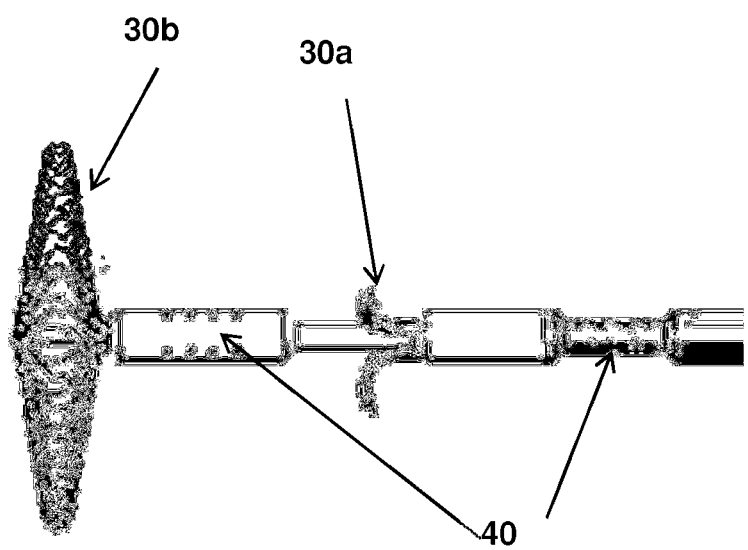
FIG. 5 is a schematic illustration of an anchoring segment comprising two tissue fixing elements and two mechanical anchoring elements.
Figure 6:
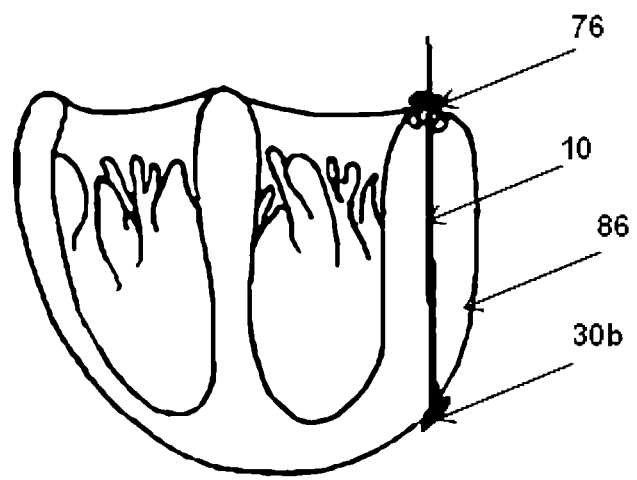
FIG. 6 is a schematic illustration of an embodiment of a muscle anchoring implant anchored in the muscle of the left ventricular of a human heart.

One or more of the mechanical anchors (30b) may be configured on a distal end of the stem to anchor to an outer surface of a muscle after the stem passes through the muscle. An example of an anchor implant comprising such a mechanical anchor is shown in FIG. 6. Such an external anchor may comprise anchoring elements (31) such as barbs, hooks, rods, bars, or combinations of these. An external mechanical anchor may additionally or alternatively comprise radially projecting members, for example as shown in FIG. 1, or a disc-shaped anchoring element as shown in FIG. 5. The radially projecting members and/or disc-shaped anchoring element may be flexible enough to adapt to an exterior surface of a muscle and or shaped to conform to the exterior surface of the muscle at an anchoring site. The disc-shaped anchor may be comprised of a braiding of memory shape material such as Nitinol or a memory shape polymer and be configured to self-expand from a collapsed delivery shape to an expanded delivered shape when released from a delivery catheter.

The anchoring segment (20) may comprise one or more tissue fixing elements (40) adapted to promote adhesion of muscle tissue to the distal anchoring segment (20). In some embodiments, holes or channels through or partially through the material of the tissue fixation section of the device allow fibrocytes and other scar tissue elements like inflammatory white blood cells to grow in or through the material in order to allow a strong fixation to tissue. In other embodiments, means for promoting the adhesion of tissue to the tissue fixing element (40) and thereby to the anchoring segment (20) may include providing a porous or microporous surface on the tissue fixing element (40) that promotes tissue migration and ingrowth into the pores. The porous or microporous surface may comprise, for example, titanium, a titanium alloy or cobalt-chrome alloy. Additionally or alternatively, the tissue fixing element (40) may comprise a coating of tissue adhesion and/or ingrowth promoter substances on its surface. Examples of tissue adhesion and/or ingrowth promoter substances may include, for example, fibronectin, collagen, fibrin, fibrinogen, TGFβ, PDGF, VEGF, bFGF, TNFα, NGF, GM-CSF, IGF-α, IL-1, IL-10, IL-8, IL-6, CTGF, and cyclosporine A. Additionally or alternatively, the tissue fixing element may comprise one or more materials that stimulate inflammation, such as carbon dust or pyrolite carbon, to promote tissue adhesion and ingrowth. In some embodiments, the tissue adhesion promoter may be a synthetic tissue of braided material or cloth made, for instance, of Dacron. The surface may also be made of a mesh of threads on the surface.

A muscle anchoring implant according to the invention may comprise one, two, three, or more tissue fixing elements (40), which may be positioned proximally or distally with respect to one or more mechanical anchors (30a, 30b). A tissue fixing element (40) may be integral with a mechanical anchor (30a, 30b) such that one or more anchoring elements (31) extend from the tissue fixing element (40) and/or one or more anchoring elements (31) are adapted to promote adhesion of muscle tissue. Embodiments comprising one or more mechanical anchors (30a, 30b) and no tissue fixing elements (40) are possible, as are embodiments comprising one or more tissue fixing elements (40) and no mechanical anchors (30a or 30b).

FIGS. 6 and 7 show embodiments of a muscle anchoring implant implanted in the left ventricle of a human heart. The embodiment shown in FIG. 6 comprises a distal mechanical anchor (30b) configured to anchor to the outside of the left ventricular muscle (86). This mechanical anchor provides immediate anchoring to allow the implant to provide a pulling force to the portion of the muscle to which the anchor (30b) is affixed. This embodiment may additionally comprise one or more tissue fixing elements (40) and or one or more mechanical anchors (30a) at the distal portion of the stem (10). Tissue fixing elements (40) provide long-term anchoring that can apply both pushing and pulling forces to the portion of the muscle to which the anchoring segment (20) is affixed. Additional mechanical anchor(s) (30a) configured to anchor inside the left ventricular muscle (86) may provide immediate anchoring that can apply pushing and/or pulling forces to the portion of the muscle to which the anchoring segment (20) is affixed. The embodiment shown also includes a proximal anchor (76) that holds a proximal portion of the stem (10) so that the stem may slide relative to the proximal anchor (76) as the left ventricle contracts and relaxes.

The position of the muscle anchor implant shown in FIGS. 6 and 7 is in the muscle of the left ventricle with the distal end near the apex of the heart and proximal anchor (76) near at the top of the left ventricle near the mitral valve annulus and the mitral valve plane. Most of the stem (10) is comprised of the adhesion resistant portion of the stem. This feature allows the muscle of the left ventricle to contract, causing the proximal end of the stem (10) to move upward and downward with respect to the proximal anchor (76).

FIG. 7 shows an embodiment in which the implant comprises a distal mechanical anchor (30b) configured to anchor inside the left ventricular muscle (86). This mechanical anchor may provide immediate anchoring to allow the implant to provide a pulling force, a pushing force, or both to the portion of the muscle to which the anchor (30b) is affixed. This embodiment may additionally comprise one or more tissue fixing elements (40) and or one or more mechanical anchors (30a) at the distal portion of the stem (10). Tissue fixing elements (40) provide long-term anchoring that can apply both pushing and pulling forces to the portion of the muscle to which the anchoring segment (20) is affixed. Additional mechanical anchor(s) (30a) configured to anchor inside the left ventricular muscle (86) may provide immediate anchoring that can apply pushing and/or pulling forces to the portion of the muscle to which the anchoring segment (20) is affixed. The embodiment shown includes an actuator (74) comprising or attached to the proximal anchor (76). This feature allows the natural movement of the left ventricular muscle (86) to be assisted by the actuator (74) applying a pushing and/or a pulling force to the proximal end of the stem (10), which is transferred by the stem (10) to the anchoring segment (20). The actuator may be, for example, a mechanical linear actuator, a hydraulic linear actuator, a piezoelectric actuator, or an electro-mechanical actuator.

The embodiments shown in FIGS. 6 and 7 exemplify the use of a muscle anchor implant of the invention in the muscle of the left ventricle with the proximal anchor (76) in or near the atrioventricular pane. In another embodiment, the orientation of the muscle anchor implant may be reversed with the distal end anchored in or on the left ventricle near the mitral valve annulus and the proximal anchor (76) on the left ventricle near the apex of the heart. In other embodiments, the anchor implant may be implanted in the right ventricle, the interceptal segment of the left ventricle, the left atrium, or the right atrium. The features of the implant, proximal anchor (76), and/or actuator (74) are also capable of application to skeletal muscles including, but not limited to, the biceps brachii, biceps femoris, brachialis, diaphragm, flexor carpi radialis, flexor carpi ulnaris, gastrocnemius, or triceps. The distal end of the anchor implant may be oriented toward the insertion of the muscle with the proximal end oriented toward the origin or vice versa. One advantage of the implant is that the length of the stem (10) and the adhesion resistant segment (14) may be chosen for insertion into a specific muscle to a specified depth and/or to provide a maximum or minimum stroke length delivered from a device providing a pulling and/or pushing force for assisting muscle contraction and/or relaxation.

The implant may be used to assist the movement of the muscle by applying a pushing and/or a pulling force to the proximal end of the stem (10), and due to the adhesion resistant segment (14) of the stem (10), allowing the muscle to slide along the stem (10), thereby causing the pushing and/or pulling force to transfer via the stem to the anchoring segment (20), and causing the assisting movement of the muscle. The muscle may be a heart muscle and the assisting movement of the muscle may be moving the implant so that the heart valves move. The assisting movement of the muscle may be moving the implant so that the heart valves coapt. Examples of assisting movement are e.g. contraction and/or extension of the muscle at the adhesion resistant segment (14), which is made possible because of the adhesion resistant properties of this segment that prevents adhesion or ingrowth of the muscle to the stem. As shown in FIGS. 6-7, the implant may be implanted so that the anchoring segment (20) is on the outer side of the muscle or inside the muscle, and at least a portion of the adhesion resistant segment (14) is inside the muscle.

The muscle anchoring implant may be implanted directly by insertion into a muscle by open surgery, or can be delivered percutaneously through a cannula, trocar, or catheter. The cannula, trocar, or catheter may have a sharp tip for penetrating muscle tissue so that the implant may be deployed inside the muscle by pushing the implant out of the cannula, trocar, or catheter. Alternatively or additionally, the implant may have a sharp distal end. Implantation of such an embodiment may include pushing the implant at least partially out of the distal end of the cannula, trocar, or catheter and pushing the cannula, trocar, or catheter into the muscle before completely releasing the implant from the cannula, trocar, or catheter. The implant may be inserted into an incision into a muscle made by a separate cutting device or, if the implant has a sharp distal end, the implant may be pushed into the muscle without making an incision first.

Some embodiments of the muscle anchor implant are designed for transvascular delivery through a catheter. A method for transvascular delivery to the site of implantation comprises percutaneously introducing a catheter into a blood vessel in fluid communication with the muscle into which the implant is to be placed. This method is particularly useful for implantation into cardiac muscle. The catheter is advanced through the vasculature to the target muscle. The implant is pushed through a catheter (68). A pushing/pulling rod (72) may be used to push the stem (10) through the catheter (68) to the site of implantation. The pushing/pulling rod (72) may be reversibly or permanently attached to a connecting element (66) on the stem (10). The catheter (68) may have a sharp tip on its distal end to penetrate through muscle tissue to so that the distal end of the stem (10) comprising the anchoring segment (20) is positioned at or near an anchoring location of the implantation site. The catheter may be advanced into the muscle all or part of the way to the anchoring location. A guide wire (25) sharp enough to pass through the target muscle and passing through a central lumen (80) of the stem (10) may be used to guide the catheter and the stem to the implantation site. In some embodiments, the anchoring elements (31) may be configured to expand automatically once they exit the catheter (68). In such embodiments, the catheter (68) may comprise a rigid section (69) at its distal end. At the site of implantation, the anchoring elements (31) are allowed to expand and, depending on the type of anchoring segment (30a, 30b), the anchoring units penetrate into the muscle tissue and/or conform to an outer surface of the muscle after exiting the rigid section (69). The rigid section (69) of the catheter (68) may be rigid enough to collapse anchoring elements (31) if they are drawn back into the catheter (68) by pulling on the stem (10). This feature allows the implant to be immediately withdrawn if a problem arises during delivery before the anchoring segment(s) becomes permanently fixed at the implantation site.

FIG. 8 shows an embodiment in which separate sections of the stem (10) are assembled inside a catheter, for example during delivery of the implant. The first section (91) comprises a connecting means (50) for connecting to a second section (92). The connecting means can be, for example, a threaded connection, Luer fitting, force fit connection, or other known connecting means used with medical devices. The connecting means (50) can be used to form a reversible or an irreversible connection between any two sections. In the embodiment shown in FIG. 8, the connecting means (50) is a threaded connector. The connecting means (50) may be covered by a protective cover (52). The protective cover (52) may be made of a biocompatible material, for example, a biocompatible polymer. The biocompatible material may be, but need not be, biodegradable and/or bioresorbable. The protective cover (52) may comprise lateral side walls rigid enough to slide over the outside of the first section (91) when pushed by the second section (92) or the side walls may have a thickness or composition that allows the cover to collapse when the second section (92) is pushed against the first section (91) (i.e. the first and second sections are pushed together). The protective cover (52) preferably comprises a proximal surface that can be disrupted by pressure applied by the second section (92) to expose a portion of the connecting means on the first section (91) to a portion of the connecting means on the second section (92). To facilitate disruption, the protective cover (52) may have a proximal side having a thinner construction than the lateral sides or a penetrable, slotted construction that allows a portion of the first section (91) and/or a portion of the second section (92) to penetrate the proximal side of the protective cover (52) when the first and second sections are pushed together. Contamination of connection surfaces may result in non-optimal connections or increase the risk of corrosion in the connecting surfaces. The protective cover (52) prevent physiological fluids from contaminating surfaces of the connection means before the surfaces come into contact or at least reduces the amount of contamination of the surfaces by minimizing the time the surfaces are exposed to physiological fluids, such as blood, interstitial fluid, and lymph.

In a method for assembling a muscle anchor implant of the type shown in FIG. 8, the first section (91) comprising the distal most portion of the anchoring segment (20) and being attached to a guide wire (25) is inserted into the catheter. The guide wire (25) may be attached to the distal end of the first section (91) and pass through a central lumen of the section. Alternatively, the guide wire (25) may be attached to the proximal end of the connecting means (50). The first section (91) is advanced through the catheter (68), which may be, but need not be, positioned at or near the implantation site.

Once the first section is positioned at a desired location within or just outside the catheter, the second section (92) is advanced over the guide wire (25) through the catheter and connected to the first section (91). Connecting the second section (92) to the first section (91) may involve twisting the first and second sections relative to one another for connecting via a threaded or Luer lock connecting means (50). This process may be repeated with one or more additional sections (93) until the entire stem (10) is assembled.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A muscle implant, said implant comprising:
a stem comprising an adhesion resistant segment and a distal anchoring segment on a distal end of the stem and a proximal anchor with self-expanding anchoring elements spaced apart from the distal anchoring segment; wherein:
at least a portion of each of said adhesion resistant segment and said distal anchoring segment is configured to be implantable within a muscle wall, said at least a portion of said adhesion resistant segment that is configured to be implantable within said muscle wall is further configured to allow relative motion between said muscle wall and said stem;
and,
said adhesion resistant segment is positioned proximally on said stem relative to said distal anchoring segment.

2. The implant of claim 1, wherein at least a portion of said stem is curved, or wherein at least a portion of said stem is flexible or conditionally flexible.

3. The implant of claim 1, wherein an outer surface of said adhesion resistant segment is comprised of polished steel or is covered by a flexible membrane or a flexible sleeve.

4. The implant of claim 1, wherein said stem is configured to be deliverable to said muscle wall through a catheter.

5. The implant of claim 1, wherein said distal anchoring segment comprises at least one mechanical anchor adapted to be anchorable to a surface of said muscle wall from outside of the muscle wall.

6. The implant of claim 1, wherein said distal anchoring segment comprises at least one mechanical anchor adapted to be anchorable to said muscle wall from inside the muscle wall.

7. The implant of claim 6, wherein said at least one mechanical anchor comprises a plurality of anchoring elements extending radially from said anchoring segment.

8. The implant of claim 7, wherein said plurality of anchoring elements are comprised of a shape memory metal and/or a super elastic material.

9. The implant of claim 6, wherein said distal anchoring segment comprises at least one tissue fixing element adapted to promote adhesion of tissue to said anchoring segment.

10. The implant of claim 9, wherein said at least one tissue fixing element comprises a porous surface configured to promote tissue ingrowth into said porous surface.

11. The implant of claim 9, wherein said at least one tissue fixing element is positioned proximally or distally to said at least one mechanical anchor in said distal anchoring segment.

12. The implant of claim 9, wherein said at least one tissue fixing element is integral with said at least one mechanical anchor.

13. The implant of claim 1, comprising a connecting element attached to a proximal portion of said stem.

14. The implant of claim 1, wherein said stem comprises a plurality of structural sections adapted to be assembled in a catheter.

15. The implant of claim 1, wherein said stem comprises a plurality of structural sections adapted to be assembled over a guide wire.

16. The implant of claim 1, wherein, when the at least a portion of the distal anchoring segment is implanted in a muscle wall, the muscle implant is configured to assist contraction and/or extension of the muscle wall when a force is applied through the stem to a portion of the muscle wall.

17. The implant of claim 16, wherein the stem is further configured so that, when the implant is implanted in the muscle wall and a force is applied to a proximal end of said stem in a direction towards a distal end portion of said stem or in a direction away from the distal end portion of said stem, the stem is configured to exert the force to the muscle wall, thereby assisting movement of the muscle wall.

18. The implant of claim 7, wherein said plurality of anchoring elements are comprised of barbs, hooks, rods, bars or combinations thereof.

* * * * *